United States Patent [19]
Deguchi et al.

[11] Patent Number: 6,063,830
[45] Date of Patent: May 16, 2000

[54] DENTAL CURABLE COMPOSITION AND ARTIFICIAL TOOTH

[75] Inventors: Mikito Deguchi, Kyoto; Hiroyuki Shioi, Higashiosaka; Akihiro Nagafuji, Kyoto, all of Japan

[73] Assignee: Kabushiki Kaisha Shofu, Kyoto, Japan

[21] Appl. No.: 08/985,193

[22] Filed: Dec. 4, 1997

[30] Foreign Application Priority Data

Dec. 6, 1996 [JP] Japan .................................. 8-326579
Dec. 6, 1996 [JP] Japan .................................. 8-326581

[51] Int. Cl.$^7$ .............................. A61K 6/083; C08K 3/34
[52] U.S. Cl. ...................... 523/115; 523/116; 523/212; 524/493; 524/534; 526/301
[58] Field of Search ...................... 523/115, 116, 523/212; 524/493, 534; 526/301

[56] References Cited

U.S. PATENT DOCUMENTS

| | | | |
|---|---|---|---|
| 3,425,988 | 2/1969 | Gorman et al. | 525/290 |
| 4,297,266 | 10/1981 | Ibsen et al. | 523/116 |
| 4,347,174 | 8/1982 | Nagase et al. | 523/116 |
| 4,396,377 | 8/1983 | Roemer et al. | 523/116 |
| 4,617,327 | 10/1986 | Podszun | 523/116 |
| 4,711,913 | 12/1987 | Tateosiaw et al. | 523/116 |
| 5,127,834 | 7/1992 | Hasegawa et al. | 523/115 |

FOREIGN PATENT DOCUMENTS

| | | |
|---|---|---|
| 0166009 | 1/1986 | European Pat. Off. . |
| 0295627 | 12/1988 | European Pat. Off. . |
| 0356868 | 3/1990 | European Pat. Off. . |
| 0363026 | 4/1990 | European Pat. Off. . |
| 48-29294 | 4/1973 | Japan . |
| 5209027 | 8/1993 | Japan . |
| 7291817 | 11/1995 | Japan . |
| 9008799 | 8/1990 | WIPO . |

*Primary Examiner*—Andrew E. C. Merriam
*Attorney, Agent, or Firm*—Stevens, Davis, Miller & Mosher, L.L.P.

[57] ABSTRACT

The present invention provides a dental curable material suitable for a production of an artificial teeth having a strong toughness, wear resistance, transparency and moldability, which comprises a silane-treated silica uniformely dispersed in urethane (meth)acrylate (a): said silica has a 1 to 85 nm, with at least one silane compound represented by the formula (1):

$$Y_nSiX_{4-n} \qquad (1)$$

wherein Y is a hydrocarbon group or a reactive group containing a vinyl-polymerizable group; X is a hydrolyzable group; and n is an integer of 1, 2 or 3, and is uniformly dispersed in a urethane (meth)acrylte (b).

19 Claims, 1 Drawing Sheet

DENTAL CURABLE COMPOSITION AND ARTIFICIAL TOOTH

BACKGROUND OF THE INVENTION

The present invention relates to a dental curable composition and an artificial tooth. More particularly, it relates to a dental curable composition having strong toughness, wear resistance, transparency, excellent adaptability/physical characteristics to intraoral long-term use and particularly excellent molding processability, which is useful in the production of an artificial tooth or a dental crown restorative material. Further, the present invention relates to materials for an artificial tooth produced therefrom and materials for the tooth excellent in moldability

PRIOR ART

As the artificial tooth and dental crown restorative resin, for example, (meth)acrylte materials represented by methyl methacrylate (hereinafter abbreviated to "MMA") and poly(methyl methacrylate) (hereinafter abbreviated to "PMMA") have hitherto been used because of their material characteristics, particularly transparency, moldability, average physical characteristics and cheap price. However, since the (meth)acrylate material is inferior in mechanical strength and wear resistance, when using as a denture, there arose a problem that wear and roughness of the material ar caused by attrition and toothbrush wear.

For the purpose of improving the wear resistance and strength, various dental composite materials prepared by packing a polymerizable monomer with an inorganic compound have hitherto been studied. In Japanese Patent Kokai Publication No. 29294/1973, for example, an artificial tooth having excellent wear resistance is obtained by blending a spherical or amorphous inorganic oxide ($SiO_2$) having a specific particle diameter (4.0 to 40 $\mu$m) with an unsaturated polyester or an ethylenically unsaturated monomer, and polymerizing the resulting blend. However, since the inorganic compound used has a large particle diameter and the polymerized surface of the resulting composite material is rough, when using the composite material intraorally, there arose a problem about contamination, aesthetic property, etc. When the amount of the inorganic compound packed was increased, the wear resistance could be improved, but the toughness was deteriorated and it was difficult to use as the artificial tooth. The polymerized article is opaque and, therefore, it was difficult to sufficiently reproduce a color tone as the artificial tooth. When a polymerizable polyfunctional monomer is particularly used in view of the material characteristics, it became difficult to bond with the (meth)acrylte material and the molding processability was inferior. Furthermore, a high-output power is required to kneading of the polymerizable polyfunctional monomer and inorganic compound and a lot of problems are still to be remained for mass production.

Japanese Patent Kokai Publication No. 291817/1995 discloses that a cured article having excellent transparency and wear resistance can be obtained by polymerizing a composition wherein a silica polymer obtained by hydrolyzing or polycondensing a specific silane compound in the presence of colloidal silica having an average particle diameter of 1 to 100 nm is dispersed and a polymerization initiator is blended. However, in this method, when PMMA is mixed with a silica dispersion and is swollen, the silica dispersed uniformly in MMA causes agglomeration sometimes. There still remained a problem that polymerized material is opaque and brittle. Furthermore, physical properties of a polymerized material of the formulation comprising 20.0 to 99.0% by weight of silica-dispersed MMA, 0.99 to 80.0% by weight of a polymer and 0 to 28.6% by weight of a polymerization initiator or a polyfunctional (meth)acrylate were not sufficient as the dental composite material because it contains MMA as a main component.

SUMMARY OF THE INVENTION

An object of the present invention is to provide a dental curable composition wherein an inorganic filler treated with a silane compound is uniformly dispersed in a fine state, thereby imparting strong toughness, wear resistance, transparency and molding processability to an artificial tooth.

The present invention provides a dental curable composition comprising a silane-treated silica uniformly dispersed in urethane (meth)acrylate (referred to as a uniformly dispersed silica (a) hereinafter) obtained by treating a colloidal silica having an average primary particle size of from 1 to 85 nm with at least one silane compound represented by formula (1):;

$$YnSiX4-N$$

wherein Y is a hydrocarbon group or a reactive group containing a vinyl polymerizable group; X is a hydrolyzable group; and n is an integer of 1, 2 or 3, and being uniformly dispersed in urethane (meth)acrylate, and an artificial teeth produced therefrom.

DETAILED DESCRIPTION OF THE INVENTION

The present invention relates to a dental curable composition comprising a silane-treated silica uniformly dispersed in urethane (meth)acrylate (referred to as uniformly dispersed silica (a) in the present specification) obtained by treating a colloidal silica having an average primary particle size of from 1 to 85 nm with at least one silane compound represented by formula (1):

wherein Y is a hydrocarbon group or a reactive group containing a vinyl polymerizable group; X is a hydrolyzable group; and n is an integer of 1, 2 or 3, and being uniformly dispersed in urethane (meth)acrylate.

The uniformly dispersed silica (a) may comprise preferably urethane (meth)acrylate 29–69% by weight, more preferably 45–65, colloidal silica 10 –70% by weight, more preferably 15–45 by weight, and silane compounds 1–30% by weight, more preferably 5–25% by weight.

The average particle size of the colloidal silica is about 1 to 85 nm, more preferably 1 to 30 nm as a primary diameter.

The dental curable composition of the present invention the urethane (meth)acrylate may contain two or more urethane groups and two or more acryloyl groups and/or methacryloyl groups in one molecule as described hereinafter.

The dental curable composition of the present invention may comprise a uniformly dispersed silica (a) 34–68% by weight, more preferably 40–68% by weight, a polymerizable monomer (b) 17–51% by weight, preferably 26–51% by weight, poly(alkyl (meth)acrylate) 15–20% by weight, preferably 17–20% by weight, and it may contain additionally a polymerization initiator (d) 0.1 to 3.0% by weight, preferably 0.3 to 1.5% by weight based on the total weight of (a), (b) and (c).

The present invention further provides a tooth or a dental crown restorative material obtained from the above dental curable composition.

Figure 1:
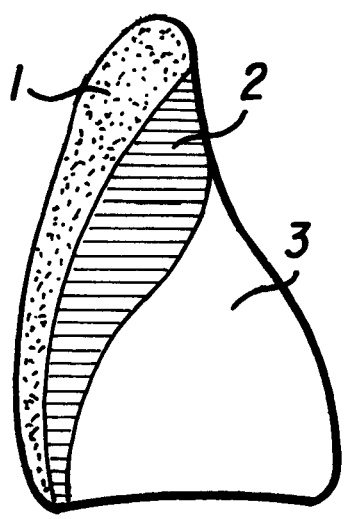
FIG. 1 is a schematic view of an anterior tooth.
Figure 2:
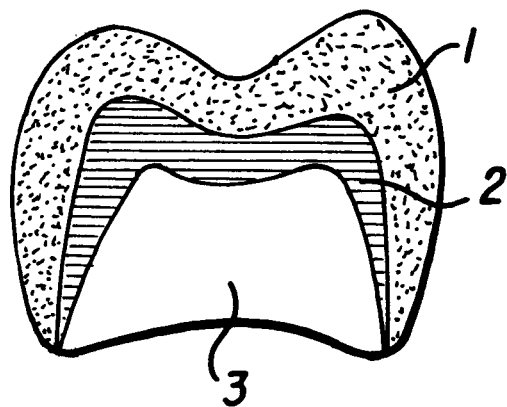
FIG. 2 is a schematic view of a molar tooth.

The present invention further provides an artificial tooth, which is shown in FIG. 1 (an anterior tooth) and FIG. 2 (a molar tooth). The artificial tooth has three portions comprise:

(A) an enamel portion (1) comprising (a) uniformly dispersed silica as aforementioned, (b) polymerizable monomers, (c) poly(alkyl (meth)acrylates), and (d) polymerization initiator, (B) a dentinal portion (2) comprising the above (b), (c), (d) and (e) one or more kinds of homogeneous compositions in which the poly(alkyl (meth)acrylates) (c) and urethane (meth)acrylates are homogeneously mixed, and (C) a base portion (3) comprising the above (b), (c) and (d).

Thus, the present invention relates to an artificial tooth composed of an enamel portion containing uniformly dispersed fine inorganic fillers treated with the silane compounds, excellent in the toughness, wear resistance, transparency and moldability; a dentinal portion comprising homogeneous compositions excellent in the toughness in which a polymer is homogeneously mixed with urethane (meth)acrylate showing neither solubility nor swelling properties to the polymer; and a base portion excellent in the adhesive properties therewith.

The artificial tooth composing of the above portions shows not only an excellent appearance, anti-shock properties but also moldability.

The homogeneous composition (e) composing of a part of the dentinal portion may be a composition obtained by reacting an isocyanate in a homogeneous solution of a poly(alkyl (meth)acrylate) (c) and a hydroxyl group-containing (meth)acrylate or a composition obtained by reacting a hydroxyl group-containing (meth)acrylate in a homogeneous solution of the poly(alkyl (meth)acrylate) (c) and an isocyanate. Or the composition (e) may be a reaction product obtained by reacting firstly a polyol having 2 to 4 hydroxyl groups in a homogeneous solution of poly(alkyl (meth)acrylate) (c) and an isocyanate and then reacting the residual isocyanate with a hydroxyl group-containing (meth) acrylate. In the present invention the poly(alkyl (meth) acrylate) (c) may be a homopolymer or a copolymer, and it is sometimes referred to as "polymer (c)" simply.

According to the above process a homogeneous composition in which a polymer (c) and an urethane (meth)acrylate showing neither solubility nor swelling properties to the polymer (c) are homogeneously mixed can be prepared.

In order to polymerize the composition of the present invention, a polymerization temperature is preferably within the range from 50 to 150° C. In this case, a peroxide catalyst is preferably added in an amount within the range from 0.1 to 3 parts by weight based on 100 parts by weight of the polymerizable compounds. In case of polymerizing by ultraviolet or visible light, an accelerator and a photosensitizer are preferably added in an amount within the range from 0.2 to 3 parts by weight based on 100 parts by weight of the dental curable composition. It is also possible to polymerize under a pressure of 50 to 400 kgf/cm², in addition to these conditions.

The feature of the present invention is as follows. That is, using a colloidal silica dispersed in a solvent, it becomes possible to disperse silica in a state that an average particle diameter is smaller than 0.1 μm, which has hitherto been considered to be difficult, and it also becomes possible to disperse silica in a matrix resin with maintaining the uniformly dispersed state. As a result, there can be provided a cured article which contains no agglomerated filler but has strong toughness, wear resistance, transparency and molding processability.

The composition of the present invention also has a feature that a finely dispersed state of silica, which has never been accomplished in case of a conventional inorganic filler-dispersed material, is stable for a long period of time.

The above feature of the present invention is obtained using a silane-treated colloidal silica and using an urethane (meth)acrylate as a polymerizable matrix in which the silane-treated colloidal silica is dispersed.

The urethane (meth)acrylate used in the present invention has at least two acryloyl groups and/or methacryloyl groups and at least two urethane groups. Examples thereof include 7,7,9-trimethyl-4,13-dioxo-3,14-dioxo-5,12-diaza-hexadecane-1,16-diol-dimethacrylate (hereinafter abreviated to "UDMA"), 1,6 bis[(2-phenoxy-2'-acryloxy) isopropyl-oxy]isopropyl-oxy-carbonylamino]hexane (hereinafter abbreviated to "UDA"), 1,1,1-tri[6[(1-acryloxy-3-phenoxy)isopropyloxycarbonylamino] hexylcarbamoyloxymethyl]propane (hereinafter abbreviated to "URO") and the like. Urethane (meth)acrylates represented by the following structural formulas:

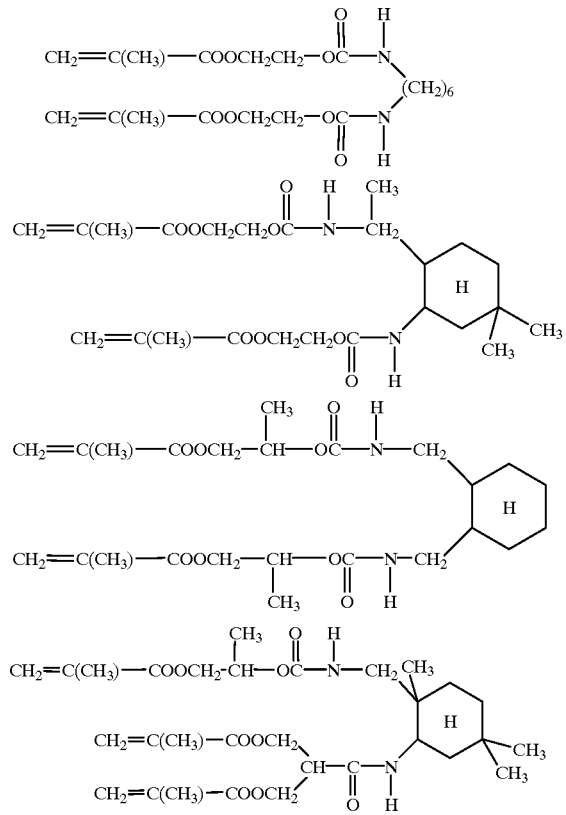

are also preferable. These urethane (meth)acrylates can be used alone or in combination thereof. The main chain of the urethane bond may contain an alifatic, aromatic or alicyclic group basically, but preferably the main chain contains neither aromatic nor alicyclic group and the side chains contain one or more alifatic, aromatic and/or alicyclic group. Particularly preferable compounds are UDMA, UDA and URO.

The term main chain "means a portion between two urethane bonds, and the term "side chain" means the portion out side of the two urethane bonds.

In the present invention, it is possible to optionally blend a monomer and/or polyfunctional monomer, which are copolymerizable with an urethane (meth)acrylate, together with the urethane (meth)acrylate. Examples of the polymerizable monomer include monofunctional monomers having one ethylenically unsaturated bond (e.g. MMA, ethyl (meth) acrylate, 2-hydroxyethylpropyl methacrylate, perfluorooctyl (meth)acrylate, hexafluorobutyl (meth)acrylate, etc.; and polyfunctional monomers having at least two ethylenically unsaturated bonds (e.g. ethylene glycol di(meth)acrylate (hereinafter abbreviated to "EG"), triethylene glycol di(meth)acrylate, butylene glycol di(meth)acrylate, trimethylolpropane trimethacrylate (hereinafter abbreviated to "TMPT"), 2,2-bis[4-methacryloxyethoxyphenyl]propane di(meth)acrylate, etc.

When the above polymerizable monomer is blended, the monofunctional monomer in the polymerizable monomer is used in an amount within the range from 20 to 50% by weight based on 40 to 80% by weight of the urethane (meth)acrylate (b), or the polyfunctional monomer is used in an amount of 20% by weight or less. In case of mixing with the poly(alkyl (meth)acrylate), when the amount of the monofunctional monomer such as MMA is smaller than 20% by weight, the molding processability is inferior. On the other hand, when the amount is larger than 50.0% by weight, physical characteristics are particularly inferior.

As the colloidal silica used for the uniformly dispersed silica(a) in the present invention, various commercially available products can be used. The preferable particle diameter of the colloidal silica is from 1 to 85 nm. As the colloidal silica, various commercially available products can be used and examples thereof include those which are sold under the trade name of Snowtex IPA-ST (manufactured by Nissan Chemical Industries, Ltd.) (hereinafter abbreviated to "IPA-ST") (average particle diameter: 10 to 15 nm), OSCAL-1432 (manufactured by Shokubai Kasei Kogyo Co., Ltd.) (average particle diameter: 10 to 20 nm) and OSCAL-1632 (manufactured by Shokubai Kasei Kogyo Co., Ltd.) (average particle diameter: 11 nm) (the term "average particle size" used herein means an average particle diameter of primary particles). The dispersion medium of the colloidal silica is not specifically limited, but water, methanol, alcohols (e.g. isopropyl alcohol, etc.), cellosolves and dimethylacetamides may be used. Particularly preferable dispersion mediums are alcohols, cellosolves and water.

The colloidal silica used in the present invention is treated with the general formula (1):

$$Y_n SiX_{4-n} \quad (1)$$

[wherein Y represents a hydrocarbon group or a reacting group containing a vinyl-polymerizable group; X represents a hydrolyzable group; and n represents an integer of 1, 2 or 3]. The examples of hydrocarbon group include an alkyl group, especially one having 1 to 3 carbon atoms, a phenyl group and the like, or a mixture thereof. The examples of reactive group containing a vinyl-polymerizable reactive group include a vinyl group, an acrylic group, a methacrylic group, and the like a mixture thereof. The hydrolyzable group has a property of eliminating in an acid catalyst, and specific examples thereof include alkoxy group, methoxyalkoxy group, acetoxy group and phenyloxy group.

Examples of the silane compound represented by the general formula (I) include methyltriethoxysilane, ethyltrimethoxysilane, phenyltrimethoxysilane, phenyltriethoxysilane, methylphenyldiethoxysilane, trimethylmethoxysilane, trimethylethoxysilane, methoxyethyltriethoxysilane, acetoxyethyltriethoxysilane, methyltriacetoxysilane, methyltris(acryloxyethoxy) silane, methyltris(methacryloxyethoxy) silane, β-methacryloxyethyldimethoxymethylsilane, γ-acryloxypropylmethoxydimethylsilane, β-methacryloxyethyldimethoxymethylsilane, γ-methacryloxypropylmethoxydimethylsilane, γ-methacryloxypropyldimethoxysilane, γ-methacryloxypropyltrimethoxysilane, vinylmethyldimethoxysilane, vinyltrimethoxysilane, vinyltriethoxysilane, p-vinylphenyldimethoxysilane and the like.

$$CH_3Si(OC_2H_5)_3 \quad (I\text{-}1)$$

$$C_6H_5Si(OCH_3)_3 \quad (I\text{-}2)$$

$$CH_2=CHSi(OC_2H_4OCH_3)_3 \quad (I\text{-}3)$$

$$CH_2=CHSi(OCH_3)_3 \quad (I\text{-}4)$$

$$CH_3=CHSi(OC_2H_5)_3 \quad (I\text{-}5)$$

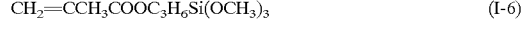
$$CH_2=CCH_3COOC_3H_6Si(OCH_3)_3 \quad (I\text{-}6)$$

The silane compounds represented by the above structural formulas are methyltriethoxysilane (I-1), phenyltrimethoxysilane (I-2), vinyltris(β-methoxyethoxy) silane (I-3), vinyltrimethoxysilane (I-4), vinyltriethoxysilane (I-5) and γ-methacryloxypropyltrimethoxysilane (I-6).

These silane compounds may be used alone or in combination thereof. Also, there may be used a silane compound wherein Y may have an alkyl group and a vinyl-polymerizable reactive group in one molecule, or used a silane compound wherein Y is an alkyl group in combination with a silane compound wherein Y is a reactive group containing a vinyl-polymerizable group. It is preferable to use the silane compound wherein Y is an alkyl group in combination with the silane compound wherein Y is a reactive group containing a vinyl-polymerizable group. More preferable one is a silane compound wherein Y is a reactive group containing vinyl-polymerizable group.

According to the silane treatment of the colloidal silica, the silane compound is hydrolyzed by an acid catalyst. In the hydrolysis reaction, a solvent can be used to perform an uniform reaction. The solvent is preferably a solvent capable of compatibilizing silane alkoxide as the reaction product with water and a catalyst. Examples of the solvent include water, methyl alcohol, ethyl alcohol, n-propyl alcohol, isopropyl alcohol, n-butyl alcohol, t-butyl alcohol, pentanol, ethylene glycol, diethylene glycol, glycerin, ethylcellosolve and the like. Among them, methyl alcohol, ethyl alcohol, n-propyl alcohol and isopropyl alcohol are particularly preferable. The silane compound in the state of being mixed with colloidal silica in the solvent is hydrolyzed at the temperature of room temperature to about 120° C., preferably about a boiling point of the solvent, for 30 minutes to 24 hours, preferably about 1 to 10 hours.

The amount of the silane compound represented by the structural formula (I-1 or I-2) is preferably from 2 to 35% by weight based on 65 to 98% by weight of the colloidal silica solid content, more preferably from 2 to 30% by weight based on 70 to 98% by weight of the colloidal silica solid content.

The amount of the silane compound represented by the structural formula (I-3, I-4, I-5 or I-6) is preferably from 2 to 35% by weight based on 65 to 98% by weight of the colloidal silica solid content, more preferably from 2 to 30% by weight based on 70 to 98% by weight of the colloidal silica solid content.

When using at least one compound represented by the structural formula (I-1 or I-2) in combination with at least one compound represented by the structural formula (I-3, I-4, I-5 or I-6), the amount of the silane compound represented by the structural formula (I-1 or I-2) is preferably from 1 to 34% by weight based on 65 to 98% by weight of the colloidal silica solid content, and the amount of the silane compound represented by the structural formula (I-3, I-4, I-5 or I-6) is preferably from 1 to 34% by weight.

The uniformly dispersed silica (a) in which a silane-treated silica is uniformly dispersed in urethane (meth) acrylate can be prepared according to the following method.

Into a dispersion of colloidal silica in a solvent a silane compound and optionally water, catalysts and the like were mixed, and the mixture is reacted under the condition as aforementioned to give a colloidal silica teated with the silane compound on their surface, and then urethane (meth) acrylate is mixed. In order to effectively perform the homogeneous dispersion a separable flask, a three neck cover, joints, a mercury seal, a stirring rod, a stirring blade, a separate funnel, a condenser, and a catch (made by Kiriyama Seisakusho) are preferably used. Then, the dispersed medium of the colloidal silica in the dispersion and hydrolyzed product of the silane compound are removed. The dispersion medium, solvent and other comparatively volatile substances are preferably removed under reduced pressure. More preferably, the volatile solvent is removed as adding dropwise urethane (meth)acrylate to the reaction system through a separating funnel. According to this process the uniformly dispersed dental curable composition of the present invention can be prepared.

In the present specification, the sentence "silane-treated silica is uniformly dispersed in urethane (meth)acrylate" means that the light transmittance of the uniformly dispersed silica (a) after or before curing is 80% or more. The light transmittance is determined by Spectrophotometer U-3200 (made by K. K. Hitachi Seisaku-sho) at 750–380 nm.

The dental curable composition of the present invention is composed mainly of the uniformly dispersed silica (a), and the elasticity and toughness of the cured products are improved more, and the moldability is extremely improved by formulating the uniformly dispersed silica (a) about 34 to 68% by weight, more preferably 40–68% by weight, the polymer (c) about 15–20% by weight, more preferably 17–20% by weight, and polymerizable monomer (b), typically MMA about 17–43% by weight, more preferably 30–43% by weight, and optionally additional polyfunctional monomer 17% by weight or less, so that the use of a high power kneader can be omitted.

The dental curable composition of the present invention can be used as an artificial tooth, a denture material or a dental restorative material after polymerizing in a suitable mold. In case of polymerizing the dental curable composition, a polymerization initiator is optionally selected according to the polymerization form suitable for each purpose. In order too polymerize the dental curable composition, a polymerization temperature is preferably within the range from 50 to 150° C. In this case, a peroxide is effective as a polymerization initiator and is added in the amount of 0.1 to 3.0 parts by weight based on 100 parts by weight of the dental curable composition. As the peroxide, lauroyl peroxide, benzoyl peroxide and 1,1-bis-t-butylperoxy cyclohexanone are preferable. In case of polymerizing by ultraviolet light and visible light, the photopolymerization initiator and reducing agent are added in the amount of 0.2 to 3.0 parts by weight based on 100 parts by weight of the dental curable composition. As the photopolymerization initiator, an $\alpha$-diketone compound, a ketal compound and an anthraquinone compound are preferable, and camphorquinone as the $\alpha$-diketone compound is particularly preferable. As the reducing agent, primary amine, secondary amine and tertiary amine are effective, and dimethylaminoethyl as the tertiary amine is particularly preferable. It is also possible to polymerized under a pressure of 50 to 400 kgf/cm$^2$, in addition to these conditions.

In the dental curing material of the present invention, there can also be blended additives such as pigments, colorants, ultraviolet absorbers, heat stabilizers, fluorescent agents, etc. as far as the effect of the present invention is not adversely affected.

Concrete examples of the polymerizable monomer (b) used for an ingredient of cured composition of the present invention is a monofunctional monomer having one ethylenically unsaturated bond, for example, MMA, ethyl (meth) acrylate, butyl (meth)acrylte, 2-hydroxyethyl methacrylate (referred to as 2-HEMA hereinafter) and the like, a polyfunctional monomer having two or more ethylenically unsaturated bonds, for example, ethylene glycol di(meth)acrylate (referred to as EG hereinafter), triethylene glycol di(meth) acrylate (referred to as TG hereinafter), trimethylol propane trimethacrylate (referred to as TMPT hereinafter), a reaction product of phosphonitrile chloride and 2-hydroxyethyl methacrylate (referred to as PPZ hereinafter), 2,2-bis[4-methacryloxyphenyl]propane di(meth)acrylate (referred to as D-2.6E hereinafter) and urethane (meth)acrylate such as UDMA and the like. Preferable compounds are MMA, 2-HEMA, EG, TG, TMPT, D-2.6E, and UDMA, and more preferable one are MMA, EG, TG and TMPT.

A poly(alkyl (meth)acrylate) which is swellable in the aforementioned monomer (b) is selected as the polymer (c) used for an ingredient of the curable composition and the enamel portion (A) of the present invention, which includes homopolymers or copolymers of PMMA, polyethyl methacrylate (referred to as PEMA hereinafter) and the like. There is included hybrid polymer particles of which core is a cross-linked poly(alkyl (meth)acrylate) and shell is one or more of the polymer of PMMA, PEMA and the like. The polymer (c) has preferably an average molecular weight of 100,000 to 1,000,000, more preferably 200,000 to 1,000,000, and an average particle size of 1 to 100 $\mu$m, more preferably 1–75 $\mu$m.

The dentinal portion (B) constituting the middle layer of the artificial tooth having three portions according to the present invention comprises monomers (b), poly(alkyl (meth)acrylate) (c), polymerization initiator (d) and one or more kinds of homogeneous composition (e) of the polymer (c) and the urethane (meth)acrylate.

The above urethane (meth)acrylates inherently show neither solubility nor swilling properties to the poly(alkyl (meth)acrylate) (c) of the present invention. The curable composition in which such an urethane (meth)acrylate and a poly(alkyl (meth)acrylate) are homogeneously mixed forms a clear mixed solution having a high viscosity, and poly (alkyl (meth)acrylate particles are not visibly observed in the solution and the poly(alkyl (meth)acrylate) is not substantially deposited with days.

The same monomer, polymer and polymerization initiator or different one as used in the enamel portion may be used for the dentinal portion. The same ones are preferably used.

In the present invention, the composition, wherein the urethane (meth)acrylate showing neither solubility nor swelling properties to the poly(alkyl methacrylate) (c) is homogeneously blended, is obtained by reacting an isocyanate compound in a homogeneous phase solution of a poly(alkyl methacrylate) (c) and a hydroxyl group-containing (meth)acrylate compound, or reacting a hydroxyl group-containing (meth)acrylate with isocyanate in a homogeneous phase solution of the polymer(c) and an isocyanate compound, in the reverse order.

In the resulting composition, the urethane (meth)acrylate is homogeneously blended at the molecular level in the poly(alkyl methacrylate) (c). Such a composition has high transparency and the cured composition has a feature such as increase in crosslink density, refining of layer structure, increase in strength of bonding between layers, etc.

The polyalkyl methacrylate used in the composition, wherein the urethane (meth)acrylate showing neither solubility nor swelling properties to the polyalkyl methacrylate is homogeneously blended, is PMMA or PEMA having an average molecular weight of 100,000 to 1,000,000 and an average particle diameter of 1 to 75 $\mu$m. It is possible to apply the method of using PEMA and PMMA to the polyalkyl methacrylate. These poly(alkyl methacrylates) can be dissolved in or swollen with any one of aliphatic isocyanates, alicyclic isocyanates and aromatic isocyanates such as hydroxyl group-containing (meth)acrylate, trimethylhexamethylene diisocyanate (hereinafter abbreviated to "TMDI"), etc. That is, the above poly(alkyl methacrylate) is homogeneously swollen or dissolved by mixing with the hydroxyl group-containing (meth)acrylate compound or isocyanate compound, thereby forming a high-viscosity transparent mixed solution.

The composition, wherein the urethane (meth)acrylate showing neither solubility nor swelling properties to the polyalkyl methacrylate is homogeneously blended, can be obtained by the following procedures. For example, a hydroxyl group-containing (meth)acrylate such as 2-HEMA, etc. is charged in a flask and, after blowing a nitrogen gas, the (meth)acrylate is heated to 40 to 50° C. With stirring at a rate of 50 to 80 rpm, a polyalkyl methacrylate is added by small portions and then completely swollen/dissolved.

Then, a tin catalyst used generally in synthesis of urethane is dissolved therein and, after dissolving, the atmosphere of the flask is replaced by an oxygen gas. With blowing this gas, an isocyanate compound such as TMDI, etc. is added dropwise over 2 to 3 hours. Normally, a slightly excess amount of the diisocyanate is used. After the completion of the dropwise addition, the mixture is heated to 70±1° C. to obtain a desired product.

The desired product can also be produced by charging TMDI in the flask, and adding a hydroxyl group containg (meth)acrylate such as 2-HEMA, in the reverse order.

When using the polyisocyanate having an isocyanate at the terminal, obtained by reacting polyol with excess diisocyanate, a polyhydrix alcohol (number of hydroxyl groups: 2 to 4) is reacted in a homogeneous phase solution of a polymer and isocyanate, and then the reactive terminal isocyanate group may be reacted with the hydroxyl group-containing (meth)acrylate.

The amount of the polymer added is suitably from 5.2 to 47 g based on 1 mol of the isocyanate compound such as UDMA, etc.

Suitable examples of the hydroxyl group-containing (meth)acrylate used in the present invention include 2-HEMA, 3-hydroxypropyl methacrylate, 4-hydroxybutyl methacrylate, 5-hydroxypentyl methacrylate, 6-hydroxyhexyl methacrylate, 2-hydroxy-3-phenyloxypropyl methacrylate (hereinafter abbreviated to "2-HPPA"), 2-hydroxyethyl acrylate, 3-hydroxypropyl acrylate, etc., preferably 2-HEMA, 2-HPPA and 3-hydroxypropyl methacrylate, more preferably 2-HEMA and 2-HPPA.

On the other hand, suitable examples of the isocyanate compound include trimethylhexamethylene diisocyanate (hereinafter abbreviated to TMDI), hexamethylene diisocyanate (hereinafter abbreviated to "HMDI"), bisphenol A diisocyanate, dicyclohexyldimethylmethane diisocyanate, isophorone diisocyanate (hereinafter abbreviated to "IPDI"), tolylene diisocyanate, sylylene diisocyanate, diphenylmethane diisocyanate, naphthalene diisocyanate, etc., preferably TMDI, HMDI and IPDI, more preferably TMDI and HMDI.

It is also possible to use a polyisocyanate having an isocyanat group at the terminal, obtained by reacting polyol with excess diisocyanate. Examples of the polyol include ethylene glycol, diethylene glycol, triethylene glycol, tetraethylene glycol, propylene glycol, 1,4-butanediol, 2,3-butanediol, 1,1,1-trimethylolpropane, glycerin, etc. As the diisocyanate, those described above may be used without causing any problem.

When the polymers constituting the enamel portion, dentinal portion and base portion are prepared respectively, polymerization initiators which are suitable for the polymerization processes for the respective polymers may be optionally selected. In order to produce the polymers for the enamel portion, dentinal portion and base portion the polymerization temperature is suitably 30 to 150° C. respectively. As the polymerization initiator peroxides are suitable, which may be used in the amount of 0.1 to 3.0 parts by weight, more preferably 0.3 to 1.5 parts by weight based on the total amount of 100 parts by weight of the uniformly dispersed silica (a), the polymerizable monomer (b) and the homogeneous composition (e) of poly(alkyl (meth)acrylate) and urethane (meth)acrylate.

As the peroxides lauroyl peroxide, benzoyl peroxide, 1,1-bit-t-butylperoxycyclohexane are preferable. In case that the polymerization is performed by ultraviolet light or visible light, a photopolymerization initiator and/or reducing agent may be used in the amount of 0.2 to 3.0% by weight based on 100 parts by weight of the total amount of the above ingredients (a), (b) and (e). As the photopolymerization initiator $\alpha$-diketone compounds such as camphor quinone (referred to as "CQ" hereinafter), ketal compounds, anthraquinone compounds and the like may be used. Particularly preferably photopolymerization initiators are CQ. As the reducing agent primary amines, secondary amines or tertiary amines are effective, especially dimethylaminoethyl methacrylate, one of the tertiary amines is preferably. The polymerization may be carried out under the pressure of 50 to 4000 kgf/cm$^2$.

Another additives such as polymerization accelerators, ultraviolet absorbing agents, fluorescences, pigments, opaquers and the like may be added in the enamel portion, dentinal portion and base portion respectively.

The present invention is illustrated by the following examples and comparative examples, but it should not be limited by these examples.

The present invention will be illustrated by the following Examples and Comparative Examples which do not limit the present invention.

Preparation of uniformly dispersed silica

Uniformly Dispersed Silica 1 (SM-1)

To 600 g of isopropyl alcohol dispersion type colloidal silica (silica content: 30% by weight) having an average particle size of 10 to 15 nm and a viscosity of 3 to 20 cps (20° C.), trade name [Snowtex IPA-ST (manufactured by Nissan Chemical Industries, Ltd.), hereinafter abbreviated to "IPA-ST"], 67.2 g of γ-methacryloxypropyltrimethoxysilane and 18.0 g of 0.01 N hydrochloric acid were added, and the mixture was heated to 70° C. One hour after heating, the reaction solution was filtered and silica deposited on the reaction solution level was removed. Then, the reaction solution was gently stirred with adding 360.0 g of UDMA and the volatile content was distilled off at 40° C. under reduced pressure to obtain a silane-treated silica uniformly dispersed in urethane (meth)acrylate (hereinafter abbreviated to "SM-1"). The transmittance at 380 to 780 nm of this composition was measured by a photometer. As a result, the composition showed the transmittance of not less than 90%. After polymerizing this composition, the transmittance was measured in the same way. As a result, it was 89.0%. This results show that the colloidal silica is dispersed uniformly as primary particles. The solid content ($SiO_2$) calculated from the ash content after calcining SM-1 in a crucible was 29.3% by weight.

Uniformly Dispersed Silica 2 (SM-2)

To 600 g of IPA-ST, 33.6 g of γ-methacryloxypropyltrimethoxysilane, 33.6 g of phenyltrimethoxysilane and 18.0 g of 0.01 N hydrochloric acid were added, and the mixture was heated to 70° C. One hour after heating, the reaction solution was filtered and silica deposited on the reaction solution level was removed. Then, the reaction solution was gently stirred with adding 360.0 g of UDMA and the volatile content was distilled off at 40° C. under reduced pressure to obtain a silane-treated silica-dispersed (uniformly) urethane (meth)acrylate (hereinafter abbreviated to "SM-2"). The transmittance at 380 to 780 nm of this composition was measured by a photometer. As a result, the composition showed the transmittance of not less than 90%. After polymerizing this composition, the transmittance was measured in the same way. As a result, it was 89.2%. This results show that the colloidal silica is dispersed uniformly as primary particles. The solid content ($SiO_2$) calculated from the ash content after calcining SM-2 in a crucible was 29.0% by weight.

EXAMPLES 1 AND 2

To SM-1 (Ex.1) and or SM-2 (Ex.2) obtained in the above 0.6% by weight of benzoyl peroxide (hereinafter abbreviated to "BPO") was added respectively and they were mixed in a mortar. After mixing, deaeration was performed in a desiccator and the atmosphere was replaced by a nitrogen gas. This operation was repeated three times. The mixture was charged in a mold so that no bubbles arise, polymerized at 75° C. under a pressure of 500 to 1000 kgf/cm² for 5 minutes and then cooled for 5 minutes. This operation was repeated twice. The polymerization was performed at 125° C. for 5 minutes, followed by polymerization at 135° C. for 10 minutes and, after the completion of the polymerization, the resultant was annealed at 100° C. for 8 hours. Then, physical characteristics such as hardness, bending strength, transmittance and wear rate were measured. The results are shown in Table 1, respectively.

EXAMPLES 3 TO 11

SM-1 or SM-2 was mixed with MMA, EG and TMPT in a proportion shown in Table 1. To the mixture, 0.6 to 1.0% by weight of BPO was added to obtain a monomer composition, respectively. Then, the monomer composition was mixed with polymethyl methacrylate (weight-average molecular weight: 400,000, average particle size: about 20 µm, hereinafter abbreviated to "PMMA-1") as a polymer in a weight ratio shown in Table 1.

As a method of mixing the monomer composition with PMMA-1, there can be used methods such as (1) mortar mixing, (2) vessel mixing, (3) ball mill mixing, etc. In the present invention, the mixing was performed using a laboratory planetary ball mill "P-5" (manufactured by Flitchu Japan Co., Ltd.). The mixing ratio is as follows: the monomer (17 g) and the polymer (3 g). The mixing conditions are as follows: room temperature, 100 rpm, mixing time of 60 minutes and 4 pebbles (10 mmφ).

After PMMA-1 was swollen, the mixture was preliminarily pressed in a mold under 20 to 80 kgf/cm² for 5 minutes, polymerized at 90° C. under a pressure of 100 to 300 kgf/cm² for 5 minutes and then cooled for 5 minutes. This operation was repeated twice. Then, the polymerization was performed at 135° C. for 10 minutes and, after the completion of the polymerization, the resultant was annealed at 100° C. for 8 hours. Then, the hardness, bending characteristics (e.g. strength, energy, modulus, etc.), transmittance and wear rate were measured. The results are shown in Table 1, respectively.

EXAMPLES 12 AND 13

The SM-1 or SM-2 (75.5% by weight) was mixed with MMA (20.0% by weight). To the resulting mixture, 1.4% by weight of dimethylaminoethyl methacrylate and 0.7% by weight of camphorquinone were added to obtain a monomer composition. Then, 80.0% by weight of the monomer composition was mixed with 20.0% by weight of PMMA-1 in the same manner as in Example 3.

After swelling, the mixture was preliminarily pressed in a mold under 20 to 80 kgf/cm² for 5 minutes. After removing an upper mold, the resultant was photopolymerized by irradiating visible light from the upper portion for 60 seconds. The evaluation was performed in the same manner as in Examples 3 to 11. The results are shown in Table 1.

Comparative Example 1

A quartz filler "Aerogyl OX-b 50" (manufactured by Nippon Aerogyl Co., Ltd., average particle diameter: 40 nm) (30% by weight) was mixed with UDMA (70% by weight) in a mortar, followed by deaeration to obtain a silica dispersion (hereinafter abbreviated to "UDM30A"). Regarding the resulting dispersion, since the quartz filler agglomerates, the dispersibility was heterogeneous. In the same manner as in Examples 1 to 11 except for using this silica dispersion in place of SM-1, a composition was produced and cured, and then evaluated in the same manner as in Examples 1 to 13. The cured article was translucent white and opaque. Regarding the physical characteristics, the bending strength and bending energy were low and the touchness was inferior. The results are shown in Table 1.

Comparative Example 2

To 30% by weight of a quartz filler "Aerogyl OX-50" (manufactured by Nippon Aerogyl Co., Ltd., average particle diameter: 40 nm), 11.2% by weight of γ-methacryloxypropyltrimethoxysilane was added, followed by mixing in a mortar. After mixing, 60% by weight of UDMA was added, followed by mixing in a mortar and further deaeration to obtain a silica dispersion (hereinafter abbreviated to "UDM30B"). Regarding the resulting dispersion, since the quartz filler agglomerates, the dispersibility was heterogeneous. In the same manner as in Examples 1 to 11 except for using this silica dispersion in place of SM-1, a composition was produced and cured, and then evaluated in the same manner as in Examples 1 to 13. The cured article was translucent white and opaque. Regarding the physical characteristics, the bending strength and bending energy were low and the toughness was inferior. The results are shown in Table 1.

Comparative Example 3

To 30% by weight of a quartz filler "Aerogyl OX-50" (manufactured by Nippon Aerogyl Co., Ltd., average particle diameter: 40 nm), 5.6% by weight of γ-methacryloxypropyltrimethoxysilane and 5.6% by weight of phenyltrimethoxysilane were added, followed by mixing in a mortar. After mixing, 60% by weight of UDMA was added, followed by mixing in a mortar and further deaeration to obtain a silica dispersion (hereinafter abbreviated to "UDM30C"). Regarding the resulting dispersion, since the quartz filler agglomerates, the dispersibility was heterogeneous. In the same manner as in Examples 1 to 13 except for using this silica dispersion in place of SM-1, a composition was produced and cured, and then evaluated in the same manner as in Examples 1 to 13. The cured article was translucent white and opaque. Regarding the physical characteristics, the bending strength and bending energy were low and the toughness was inferior. The results are shown in Table 1.

Comparative Example 4

To 30% by weight of a quartz filler "Aerogyl OX-50" (manufactured by nippon Aerogyl Co., Ltd., average particle diameter: 40 nm), 11.2% by weight of γ-methacryloxypropyltrimethoxysilance was added and a silane treatment was performed by a normal method and, furthermore, 60% by weight of UDMA was added. After mixing in a mortar, the deaeration was performed to obtain a silica dispersion (hereinafter abbreviated to "UDM30D"). In the same manner as in Examples 1 to 9 except for using this silica dispersion in place of SM-1, a composition was produced and cured, and then evaluated in the same manner as in Examples 1 to 9. The cured article was translucent white and opaque. The results are shown in Table 1.

TABLE 1

| | Monomer composition (% by weight) | | | | | Polymer (% by weight) | Hardness | Bending characteristics | | Transmittance | Wear rate |
|---|---|---|---|---|---|---|---|---|---|---|---|
| | MMA | EG | TMPT | SM-1 | SM-2 | PMMA-1 | Knoop | Strength MPa | Energy g-cm | % | % |
| Example 1 | | | | 100 | | 0.0 | 31.2 | 112.53 | | 89.0 | 0.35 |
| Example 2 | | | | | 100 | 0.0 | 31.2 | 114.26 | | 89.2 | 0.34 |
| Example 3 | 25.5 | | | 59.5 | | 15.0 | 20.5 | 128.44 | 611.10 | 80.5 | 1.23 |
| Example 4 | 17.0 | | | 68.0 | | 15.0 | 20.9 | 124.84 | 570.19 | 80.3 | 1.26 |
| Example 5 | 25.5 | | | | 59.5 | 15.0 | 20.9 | 122.45 | 550.25 | 84.3 | 1.11 |
| Example 6 | 25.5 | | | 34.0 | 25.5 | 15.0 | 19.4 | 120.63 | 594.66 | 84.5 | 1.25 |
| Example 7 | 17.0 | | | 34.0 | 34.0 | 15.0 | 22.0 | 129.89 | 642.31 | 84.6 | 1.19 |
| Example 8 | 17.0 | | | 51.0 | 17.0 | 15.0 | 20.9 | 122.45 | 550.25 | 84.3 | 1.24 |
| Example 9 | 42.5 | | 8.5 | 34.0 | | 15.0 | 21.9 | 119.73 | 540.06 | 84.3 | 1.38 |
| Example 10 | 42.5 | | 8.5 | | 34.0 | 15.0 | 22.0 | 119.50 | 500.25 | 84.9 | 1.30 |
| Example 11 | 25.5 | 8.5 | 8.5 | 42.5 | | 15.0 | 22.2 | 110.50 | 355.62 | 83.3 | 1.11 |
| Example 22 | 20.0 | | | 60.0 | | 20.0 | 20.5 | 122.45 | 543.26 | 81.2 | 1.35 |
| Example 13 | 20.0 | | | | 60.0 | 20.0 | 20.8 | 121.02 | 520.25 | 80.0 | 1.38 |
| Comparative Example 1 | 25.5 | | | UDM30A 59.5 | | 15.0 | 20.8 | 73.61 | 86.65 | 67.9 | 2.75 |
| Comparative Example 2 | 25.5 | | | UDM30B 59.5 | | 15.0 | 20.9 | 75.45 | 90.24 | 65.6 | 2.05 |
| Comparative Example 3 | 25.5 | | | UDM30C 59.5 | | 15.0 | 20.2 | 72.40 | 84.35 | 65.8 | 1.95 |
| Comparative Example 4 | 25.5 | | | UDM30D 59.5 | | 15.0 | 21.2 | 103.02 | 206.82 | 55.1 | 1.97 |

Comparative Examples 5 to 13

The silica dispersion prepared in the same manner as in Reference Example 1 described in Japanese Patent Kokai Publication No. 291817/1995 (hereinafter abbreviated to "MMA50"), EG, TMP and UDMA were mixed in a proportion shown in Table 2, and then 0.6% by weight of BPO was added in the mixture to obtain a monomer composition. The monomer composition was mixed with a polymer, polymethyl methacrylate "Acrycon AC" (manufactured by Mitsubishi Rayon Co., Ltd., hereinafter abbreviated to "PMMA-2") or a polymer, polymethyl methacrylate (weight-average molecular weight: 1,000,000, average particle diameter: about 8 μm) hereinafter abbreviated to "PMMA-3") in a weight shown in Table 2.

Method for preparation of silica dispersion (MMA50)

To 200 g of a colloidal silica dispersed in isopropyl alcohol (trade name: OSCAL-1432, manufactured by Shokubai Kasei Kogyo Co., Ltd.) (silica content: 30% by weight, average particle diameter: 15 nm), 5.2 g of trimethylmethoxysilane and 5.0 g of an aqueous 0.01 N hydrochloric acid solution were added, followed by heating to 50° C. One hour after heating, methyl methacrylate was added and MMA was added at the same rate as a distillation-off rate of the volatile component while distilling off the volatile component at 40° C. under reduced pressure using a rotary evaporator. Finally, a solvent was completely substituted with MMA to make 120 g in the total weight, followed by concentration to obtain a silica dispersion (MMA50).

After PMMA-2 was swollen with the monomer, the composition was preliminarily pressed in a mold under 20 to 80 kgf/cm$^2$ for 5 minutes, polymerized at 80° C. under 100 to 300 kgf/cm$^2$ for 5 minutes and then cooled for 5 minutes. This operation was repeated twice. Then, the polymerization was performed at 120° C. under the same pressure for 10 minutes and, after the completion of the polymerization, the resultant was annealed at 100° C. for 8 hours. Then, the hardness, bending characteristics (e.g. strength, energy, etc.), transmittance and wear rate were measured. The results are shown in Table 2, respectively.

In all Comparative Examples 5 to 13, the bending strength an bending energy were low and the toughness was inferior. The cured article was opaque.

kind of tool brush: Between (manufactured by Sunstar Co., Ltd.), size of sample: 15 mm in length×20 mm in width×2.5 mm in thickness, number of samples: 4, load: 185 g, dentifrice: toothpaste Green Sunstar, number of brushing: 30,000.

Evaluation as artificial tooth

EXAMPLES 14 TO 24

To 99.9% by weight of a mixture of the monomer composition of Examples 3 to 13 and PMMA-1, 0.1% by weight of a pigment was added, followed by mixing using a laboratory planetary ball mill to prepare a composition, respectively. After PMMA-1 was swollen with the monomer, the composition was molded and simultaneously polymerized in a T5 central incisor tooth mold for a rigid resin anterior tooth "Endula Anterio" (manufactured by Shofu Co., Ltd.). Burr correction of the molded tooth was performed to obtain an artificial tooth. This artificial tooth was bonded with a denture base resin "base resin Urban" (manufactured by Shofu Co., Ltd.) and the strength of

TABLE 2

| | Monomer composition (% by weight) | | | | Polymer | Hard- | Bending characteristics | | Trans- | Wear |
|---|---|---|---|---|---|---|---|---|---|---|
| | MMA 50 | EG | TMPT | UDMA | (% by weight) | ness Knoop | Strength MPa | Energy g-cm | mittance % | rate % |
| Comparative Example 5 | 50.0 | | | | PMMA-2 (50.0) | 18.3 | 50.95 | 44.81 | 70.3 | 2.23 |
| Comparative Example 6 | 50.0 | | | | PMMA-3 (50.0) | 18.0 | 80.79 | 133.93 | 66.3 | 2.41 |
| Comparative Example 7 | 40.0 | | | 10.0 | PMMA-2 (50.0) | 19.3 | 62.38 | 64.30 | 66.4 | 2.55 |
| Comparative Example 8 | 40.0 | | | 10.0 | PMMA-3 (50.0) | 18.6 | 92.60 | 167.57 | 65.7 | 2.41 |
| Comparative Example 9 | 25.0 | 1.7 | | 6.7 | PMMA-2 (66.7) | 17.3 | 76.77 | 100.95 | 65.0 | 2.58 |
| Comparative Example 10 | 37.5 | 2.5 | | 5.0 | PMMA-3 (50.0) | 19.7 | 89.97 | 186.82 | 65.5 | 2.35 |
| Comparative Example 12 | 23.3 | 3.3 | | 6.7 | PMMA-2 (66.7) | 17.3 | 70.66 | 75.25 | 66.0 | 2.45 |
| Comparative Example 13 | 35.0 | | 5 | 10.0 | PMMA-3 (50.0) | 21.4 | 92.09 | 163.61 | 68.8 | 2.05 |

Evaluation of the molded material

Measurement of hardness

The Knoop hardness after storage in water at 50° C. for 24 hours was measured by using a hardness tester DMH-2 (manufactured by Matsuzawa Seiki Co., Ltd.). The load was 25 g.

Measurement of bending strength

A sample (2 mm in width×2 mm in thickness×25 mm in length) was made, using a autograph AG5000B (manufactured by Simazu seisaku-sho), and the strength (maximum bending strength) and energy (shattering energy) after storage in water at 50° C. for 24 hours were measured. The number of sample was 5. The measuring conditions were as follows: a distance between the supports: 20 mm, cross-head speed: 1 mm/min.

Transmittance

The transmittance of the test piece (diameter 40 mm, Thickness 3 mm) was measured at the wavelength within the range from 780 to 380 nm, using a spectrophotometer U-3200 (manufactured by Hitachi Corp.).

Abrasion amount

The abrasion amount after the tooth brush abrasion test was measured. The measuring conditions were as follows:

bonding between the base resin and artificial tooth was determined and the repeating impact strength test of the artificial tooth was performed. The results are shown in Table 3.

In the bonding strength test, the strength of the bonding between the base resin and artificial tooth was measured by the method defined in 7.5. bonding test of JIS T6506 resin tooth. The results are shown in Table 3.

Comparative Examples 14 to 17

Using a mixture of the monomer composition of comparative examples 2 to 5 shown in Table 1 and PMMA-1, an artificial tooth was produced in the same manner as in Examples 14 to 24, and evaluated in the same manner as in Examples 14 to 24, respectively. The results are shown in Table 3.

TABLE 3

| | Bonding strength (kgf) | Impact strength (score) |
|---|---|---|
| Example 14 | 22.5 | 27.6 |
| Example 15 | 24.5 | 26.9 |

TABLE 3-continued

|  | Bonding strength (kgf) | Impact strength (score) |
|---|---|---|
| Example 16 | 22.5 | 27.5 |
| Example 17 | 24.5 | 28.4 |
| Example 18 | 23.6 | 27.5 |
| Example 19 | 25.0 | 27.0 |
| Example 20 | 24.5 | 27.6 |
| Example 21 | 23.0 | 27.4 |
| Example 22 | 24.5 | 28.5 |
| Example 23 | 24.3 | 27.5 |
| Example 24 | 24.6 | 27.0 |
| Comparative Example 14 | 20.5 | 17.5 |
| Comparative Example 15 | 21.5 | 18.5 |
| Comparative Example 16 | 21.3 | 18.5 |
| Comparative Example 17 | 22.5 | 22.0 |
| JIS value | 11.0 or more | — |
| Commercially available product (resin tooth manufactured by shofu Co., Ltd.) | 15.1 | 21.3 |

Evaluation method of artificial tooth

Boning test

The strength of bonding between the artificial tooth and resin material for dental base was measured by the method defined in 7.5 (bonding test) of JIS T6506 (resin tooth). The results are shown in Table 3.

The cutting enamel portion of the lingual surface side of the artificial tooth produced by the method defined in 7.5 (bonding test) of JIS T6506 (resin tooth) was cut vertically to the main axis, and a stainless steel bar having a diameter of 1 mm was repeatedly dropped on the center portion from the position with the height of 10 mm. Then, the impact strength of the artificial tooth was evaluated by the number of dropping and dropping load. The method of calculating scores is shown below.

The first load and number of loading (100 g×1000 times)

The second load and number of loading (150 g×1000 times)

The third load and number of loading (200 g×1000 times)

Regarding the calculation of the impact strength, the total of numerical values obtained by dividing the number of impact at each stage by 100 was taken as a score. For example, the maximum impact strength becomes (1000/100+ 1000/100+1000/100=30) if the artificial tooth is not broken after repeating impact of each 1000 times under the load of 100, 150 and 200 g.

Evaluation of molding processability (moldability) of artificial tooth

EXAMPLES 25 TO 27

Using an anterior tooth mold (T5 central incisor tooth) for a rigid resin tooth "Endula" (manufactured by Shofu Co., Ltd.), the mixtures obtained in Examples 3, 6 and 9 were subjected to a molding test respectively. Regarding the molding method, the mixture was used in the enamel portion and a mixture of MMA and PMMA was used in both dentinal and base portions, that is, three-layer molding was performed. The molding was performed in the enamel portion, dentinal portion and base portion in order. The moldability was confirmed by examining formation of crack and white turbidity of the enamel portion as well as bonding between the enamel portion and dentinal portion with changing the temperature of molding at the enamel portion. As a result, the moldability was excellent. The molding conditions and results are shown in Table 4.

In the bonding test, the bonding between the enamel portion an dentinal portion was confirmed by the repeating impact test of the artificial tooth. A repeating strength test of the artificial tooth was also performed. The measurement was performed after storage in water at 50° C. for 7 days.

Comparative Examples 18 to 21

Using the mixture obtained in Comparative Examples 1 to 4, an artificial tooth was produced in the same manner as in Examples 25 to 27 and then evaluated in the same manner as in Examples 25 to 27, respectively. The results are shown in Table 4.

TABLE 4

|  | Molding conditions | | | Moldability (ratio of number of defective moldings to number of moldings) | |
|---|---|---|---|---|---|
|  | E | D | B | Number of teeth wherein crack and white turbidity arose | Number of teeth wherin defective bonding arose |
| Example 25 | 70° C.-5 min. | 70° C.-5 min. | 135° C.-10 min. | 0/28 | 0/28 |
|  | 75° C.-5 min. | 75° C.-5 min. | 135° C.-10 min. | 0/28 | 0/28 |
|  | 80° C.-5 min. | 80° C.-5 min. | 135° C.-10 min. | 0/28 | 0/28 |
|  | 85° C.-5 min. | 85° C.-5 min. | 135° C.-10 min. | 0/28 | 0/28 |
|  | 90° C.-5 min. | 90° C.-5 min. | 135° C.-10 min. | 0/28 | 0/28 |
| Example 26 | 70° C.-5 min. | 70° C.-5 min. | 135° C.-10 min. | 0/28 | 0/28 |
|  | 75° C.-5 min. | 75° C.-5 min. | 135° C.-10 min. | 0/28 | 0/28 |
|  | 80° C.-5 min. | 80° C.-5 min. | 135° C.-10 min. | 0/28 | 0/28 |
|  | 85° C.-5 min. | 85° C.-5 min. | 135° C.-10 min. | 0/28 | 0/28 |
|  | 90° C.-5 min. | 90° C.-5 min. | 135° C.-10 min. | 0/28 | 0/28 |
|  | 70° C.-5 min. | 70° C.-5 min. | 135° C.-10 min. | 0/28 | 0/28 |
| Example 27 | 70° C.-5 min. | 70° C.-5 min. | 135° C.-10 min. | 0/28 | 0/28 |
|  | 75° C.-5 min. | 75° C.-5 min. | 135° C.-10 min. | 0/28 | 0/28 |
|  | 80° C.-5 min. | 80° C.-5 min. | 135° C.-10 min. | 0/28 | 0/28 |
|  | 85° C.-5 min. | 85° C.-5 min. | 135° C.-10 min. | 0/28 | 0/28 |
|  | 90° C.-5 min. | 90° C.-5 min. | 135° C.-10 min. | 0/28 | 0/28 |
|  | 70° C.-5 min. | 70° C.-5 min. | 135° C.-10 min. | 0/28 | 0/28 |
| Comparative Example 18 | 70° C.-5 min. | 70° C.-5 min. | 135° C.-10 min. | 9/28 | 0/28 |
|  | 75° C.-5 min. | 75° C.-5 min. | 135° C.-10 min. | 7/28 | 0/28 |
|  | 80° C.-5 min. | 80° C.-5 min. | 135° C.-10 min. | 4/28 | 3/28 |

TABLE 4-continued

| | Molding conditions | | | Moldability (ratio of number of defective moldings to number of moldings) | |
|---|---|---|---|---|---|
| | E | D | B | Number of teeth wherein crack and white turbidity arose | Number of teeth wherin defective bonding arose |
| | 85° C.-5 min. | 85° C.-5 min. | 135° C.-10 min. | 5/28 | 4/28 |
| | 90° C.-5 min. | 90° C.-5 min. | 135° C.-10 min. | 9/28 | 13/28 |
| Comparative Example 19 | 70° C.-5 min. | 70° C.-5 min. | 135° C.-10 min. | 9/28 | 0/28 |
| | 75° C.-5 min. | 75° C.-5 min. | 135° C.-10 min. | 8/28 | 0/28 |
| | 80° C.-5 min. | 80° C.-5 min. | 135° C.-10 min. | 2/28 | 6/28 |
| | 85° C.-5 min. | 85° C.-5 min. | 135° C.-10 min. | 4/28 | 4/28 |
| | 90° C.-5 min. | 90° C.-5 min. | 135° C.-10 min. | 8/28 | 14/28 |
| Comparative Example 20 | 70° C.-5 min. | 70° C.-5 min. | 135° C.-10 min. | 6/28 | 0/28 |
| | 75° C.-5 min. | 75° C.-5 min. | 135° C.-10 min. | 8/28 | 0/28 |
| | 80° C.-5 min. | 80° C.-5 min. | 135° C.-10 min. | 5/28 | 3/28 |
| | 85° C.-5 min. | 85° C.-5 min. | 135° C.-10 min. | 4/28 | 4/28 |
| | 90° C.-5 min. | 90° C.-5 min. | 135° C.-10 min. | 7/28 | 11/28 |
| Comparative Example 21 | 70° C.-5 min. | 70° C.-5 min. | 135° C.-10 min. | 5/28 | 0/28 |
| | 75° C.-5 min. | 75° C.-5 min. | 135° C.-10 min. | 5/28 | 0/28 |
| | 80° C.-5 min. | 80° C.-5 min. | 135° C.-10 min. | 3/28 | 4/28 |
| | 85° C.-5 min. | 85° C.-5 min. | 135° C.-10 min. | 3/28 | 4/28 |
| | 90° C.-5 min. | 90° C.-5 min. | 135° C.-10 min. | 4/28 | 8/28 |

Abbreviations in Table 4
E: Ename portion
D: Dentinal portion
B: Base portion

[Evaluation of dental crown restorative material]

EXAMPLE 28

The SM-1 or SM-2 (75.0% by weight) was mixed with MMA (25.0% by weight). To the mixture, 1.4% by weight of dimethylaminoethyl methacrylate and 0.7% by weight of camphorquinone were added to obtain a monomer composition. Then, 80.0% by weight of the resulting monomer composition was mixed with 19.9% by weight of PMMA-1 and 0.1% by weight of a pigment, using the same mixer as that in Example 3.

After PMMA-1 was swollen with the monomer composition, the composition was pressed in an anterior tooth mold (T5 central incisor canine) for a rigid resin tooth "Endula" (manufactured by Shofu Co., Ltd.) under 20 to 80 kgf/cm$^2$ for 5 to 19 minutes. After pressing, an upper mod was removed and visible light was irradiated from the upper portion for 120 seconds to prepare a shell. The resulting shell was bonded to an abutment according to a normal dental method. Both aesthetic property and bonding property were excellent.

[Preparation of a homogeneous composition containing a poly(alkyl (meth)acrylate) and an urethan (meth)acrylate]

(1) A homogeneous Composition 1 (B-1):

2-HEMA (260.3 g, 2 mol) was charged in a glass flask equipped with a stirring blade, and then heated to 40 to 50° C. with blowing a nitrogen gas. With stirring at a rate of 50 to 80 rpm, 5.2 g of PMMA was added gradually over 3 to 5 hours and completely swelled and dissolved. To the resulting solution, 110 mg of dibutyltin dilaurate was added. After the completion of the addition, blowing of the nitrogen gas was terminated and the atmosphere in the flask was replaced by oxygen. With passing through an oxygen, gas, TMDI (210.3 g, 1 mol) was added dropwise over 2 hours. After the completion of the dropwise addition, the mixture was heated to 70±1° C. and the addition reaction was continued until all isocyanate groups were reacted to obtain a curable composition (hereinafter abbreviated to "B-1"). The reaction end point was confirmed by the isocyanate equivalent titration method. The yield was 98.6%.

The reaction end point according to the isocyanate equivalent titration method was measured by the following method. (1) Weigh accurately 3 g of a sample and transfer to a glass-stoppered conical flask. (2) Add properly 50 ml of di-n-butylamine solution to the sample and allow to stand for 15 minutes. (3) After adding 20 ml of the first grade reagent, isopropyl alcohol, add 3 to 4 drops of a bromocresol green indicator (add 1.5 ml of a N/10 sodium hydroxide solution to 0.1 g of bromocresol green, grind sufficiently to dissolve the bromocresol green, and add water to make 100 ml), and mix sufficiently. (4) Then, titrate with N/2 hydrochloric acid. At about the end point, add N/2 hydrochloric acid drop by drop and continue the titration with shaking the solution every time. Take the point, where a blue or bluish violet color disappear and the produced yellow color continues at least 15 seconds, as the end point. In this test, perform a blank test under the same conditions.

$$\text{Isocyanate equivalent} = \frac{(B - A) \times f}{2 \times S}$$

where:
A: amount (ml) of a N/2 hydrochloric acid standard solution used in a run proper
B: amount (ml) of a N/2 hydrochloric acid standard solution used in a blank test
f: factor of a N/2 hydrochloric acid standard solution
S: amount (g) of a sample collected (2) A Homogeneous Composition 2 (B-2)

According to the same manner as that described in B-1 except for changing the amount of PMMA to 9.4 g, a composition (hereinafter abbreviated to "B-2") was obtained (yield 99.5%).

(2) A Homogeneous Composition 3 (B-3)

According to the same manner as that described in B-1 except for using 5.2 g of PEMA in place of PMMA, a composition (hereinafter abbreviated to "B-3") was obtained (yield 99%).

(4) A Homogeneous Composition 4 (B-4)

According to the same manner as that described in B-3 except for using 9.4 g of PEMA, a composition (hereinafter abbreviated to "B-4") was obtained (yield 98%).

(5) A Homogeneous Composition 5 (B-5)

TMDI (210.3 g, 1 mol) was charged in a glass flask equipped with a stirring blade, and then heated to 40 to 50° C. with blowing a nitrogen gas. With stirring at a rate of 50 to 80 rpm, 9.4 g of PEMA was added by several portions over 3 to 5 hours and completely swelled/dissolved.

To the resulting solution, 110 mg of dibutyltin dilaurate was added. After the completion of the addition, blowing of the nitrogen gas was terminated and the atmosphere in the flask was replaced by oxygen. With passing through an oxygen gas, 2-HEMA (260.3 g, 2 mol) was added dropwise over 2 hours. After the completion of the dropwise addition, the mixture was heated to 70±1° C. and the addition reaction was continued until all isocyanate groups were reacted. The reaction end point was confirmed by FT-IR and isocyanate equivalent titration method to obtain a homogeneous composition containing a poly(alkyl methacrylate) and urethane (meth)acrylate (hereinafter abbreviated to "B-5") (yield 98.2%).

(6) A Homogeneous Composition 6 (B-6)

According to the same manner as that described in B-5 except for using 47 g of PEMA, a composition (hereinafter abbreviated to "B-6") was obtained (yield 98%).

(7) A Homogeneous Composition 7 (B-7)

HMDI (168.20 g, 1 mol) was charged in a glass flask equipped with a stirring blade, and then heated to 40 to 50° C. with blowing a nitrogen gas. With stirring at a rate of 50 to 80 rpm, 10 g of PEMA was added by several portions over 3 to 5 hours and completely swelled/dissolved. To the resulting solution, 110 mg of dibutyltin dilaurate was added. After the completion of the addition, blowing of the nitrogen gas was terminated and the atmosphere in the flask was replaced by oxygen. With passing through an oxygen gas, 2-HFPA (444.5 g, 2 mol) was added dropwise over 2 hours. After the completion of the dropwise addition, the mixture was heated to 50±1° C. and the addition reaction was continued until all isocyanate groups were reacted to obtain 1,6-[(2-phenoxy-2'-acryloxy)isopropyl-oxy-carbonylamino] hexane (hereinafter abbreviated to "UDA"). The reaction end point was confirmed by FT-IR and isocyanate equivalent titration method to obtain a homogeneous composition containing a poly(alkyl (meth)acrylate) and an urethane (meth) acrylate (hereinafter abbreviated to "B-7").

(8) A Homogeneous Composition 8 (B-8)

HMDI (504.6 g, 3 mol) was charged in a glass flask equipped with a stirring blade, and then heated to 40 to 50° C. with blowing a nitrogen gas. With stirring at a rate of 50 to 80 rpm, 9 g of PEMA was added by several portions over 3 to 5 hours and completely swelled/dissolved.

To the resulting solution, 10 mg of dibutyltin dilaurate was added. After the completion of the addition, blowing of the nitrogen gas was terminated and the atmosphere in the flask was replaced by oxygen. With passing through an oxygen gas, trimethylolpropane (hereinafter abbreviated to "TMP") (134.18 g, 1 mol) was added dropwise over 2 hours. After the completion of the dropwise addition, the mixture was heated to 50±1° C. and the addition reaction between one isocyanate of HMDI and TMP was performed.

After the completion of the addition reaction, 110 mg of dibutyltin dilaurate was added. After the completion of the addition, 2-HFPA (666.75 g, 3 mol) was added dropwise over 2 hours. After the completion of the dropwise addition, the mixture was heated to 70±1° C. and the addition reaction was continued until all isocyanate groups were reacted to obtain trifunctional urethane acrylate oligomer 1,1,1-tri[6 [(1-acryloxy-3-phenoxy) isopropyloxycarbanylamino]-hexylcarbamoyloxymethyl]propane (hereinafter abbreviated to "URO"). The reaction end point was confirmed by FT-IR and isocyanate equivalent titration method to obtain a homogeneous composition containing a poly (alkyl (meth) acrylate) and an urethane (meth)acrylate (hereinafter abbreviated to "B-8") was obtained (yield 98.5%).

The homogeneous composition B-1 to B-8 were respectively confirmed by measuring each characteristic absorption using FT-IR (FT-300) (manufactured by Horiba, Ltd.) and measuring the average molecular weight and retention time of the polymer as well as those of the urethane monomer using GPC.

Examples of Formulation for Enamel Portion

EXAMPLES 29–30

The obtained uniformly dispersed silica (a) (SM-1 or (SM-2), monomers (b) (MMA and TMPT), and benzoyl peroxides (referred to as BPO) were mixed in the ratio shown in Table 5 together with a small amount of coloring agents. The mixture was deaired in a desiccator and replaced with nitrogen gas. The treated mixture (c) and poly(methyl methacrylate) (average molecular weight: 1,000,000 and an average particle size: about 8 $\mu$m, referred to as PMMA-1 hereinafter) were mixed according to the weight ratio shown in Table 5.

TABLE 5

| | components in enamel portion (parts by weight) | | | | | |
|---|---|---|---|---|---|---|
| | SM[1)] | | monomer | | | |
| Examples | SM-1 | SM-2 | MMA | TMPT | BPO | PMMA-1 |
| 29 | 40.0 | | 50.0 | 10.0 | 0.6 | 100.0 |
| 30 | | 40.0 | 50.0 | 10.0 | 0.6 | 100.0 |

1) silane-treated silica uniformly dispersed in urethame (meth)acrylate

The method of mixing the mixture (c) and PMMA-1 may be 1) mixture in a mortan, 2) agitation in a vessel, 3) milling in a ball mill and the like. In these examples the mixing was performed by a planetary ball mill for experiment P-5 (available from—Frits Japan K. K.—). The mixing ratio was the mixture (c) 15 g and PMMA-1 15 g at room temperature and at 100 rpm for 60 minutes, and using four balls (19 mm φ).

Examples Formulation of Dentinal Portion

EXAMPLES 21–40

(e) The homogeneous composition of the polymer (c) and urethane (meth)acrylate (B-1–B10), polymerized monomers (b) (MMA and TMPT), and benzoyl peroxide (BPO) were mixed in the ratio of Table 6 together with coloring agents. The mixture was deaired as replacing the nitrogen gas in a desiccator. The mixture was then mixed with the above PMMA-1 in the weight ration of Table 6.

The mixture and PMMA-1 were mixed by the same manner as in Examples 29 and 30.

TABLE 6

| | components in dentinal portion (parts by weight) | | | | | | |
|---|---|---|---|---|---|---|---|
| | B1~B10[2] | | monomer | | | | |
| Examples | kinds | content | MMA | TMPT | EG | BPO | PMMA-1 |
| 31 | B1 | 40.0 | 50.0 | 10.0 | — | 0.6 | 100.0 |
| 32 | B2 | 40.0 | 50.0 | 7.5 | 2.5 | 0.6 | 100.0 |
| 33 | B3 | 40.0 | 50.0 | 10.0 | — | 0.6 | 100.0 |
| 34 | B4 | 40.0 | 50.0 | 10.0 | — | 0.6 | 100.0 |
| 35 | B5 | 40.0 | 50.0 | 10.0 | — | 0.6 | 100.0 |
| 36 | B6 | 40.0 | 50.0 | 7.5 | 2.5 | 0.6 | 100.0 |
| 37 | B7 | 40.0 | 50.0 | 10.0 | — | 0.6 | 100.0 |
| 38 | B8 | 40.0 | 50.0 | 10.0 | — | 0.6 | 100.0 |
| 39 | B9 | 40.0 | 50.0 | 2.5 | 7.5 | 0.6 | 100.0 |
| 40 | B10 | 40.0 | 50.0 | 10.0 | — | 0.6 | 100.0 |

2) curable composition which urethane (meth)acrylate showing neither solubility nor swelling properties to poly(alkyl (meth)acrylate) is homogeneously mixed with the poly(alkyl (meth)actylate).

Examples of Formulation for Base Portion

The monomer (b) MMA 4.875 g and EG 0.125 g, BPO (d) 0.025 g and poly(methyl (meth)acrylate) 10.0 g (average molecular weight 800,000, average particle size 40 μm, and referred to as PMMA-2) were mixed.

Evaluation as Artificial Tooth

EXAMPLE 41–60

Artificial teeth were prepared using compositions for the enamel portion of the Examples 29–30, the compositions of the dentinal portion of the Examples 3–12 and the compositions for the base portion by a C5 central incisor tooth mold for a hard resin tooth "Endualanterio" (available from Shofu). The first molding was performed by polymerizing the raw materials for the enamel portion under a pressure of 750–3000 Kgf/cm² at 60–94° C. for 5 minutes and then cooled for 5 minutes; and polymerizing the raw materials for the dentinal portion under 750–3000 kgf/cm² at 60–95° C. for 5 minutes, and then cooled for 5 minutes, and finally polymerizing the raw materials for the base portion under 750° C. to 3000 Kgf/cm² at 105 to 125° C. for 5 minutes, cooled for 5 minutes, and then taken out from the mold. The obtained artificial teeth are excellent in the transparency and the appearance.

After the polymerization the artificial teeth were annealed at 100° C. for 8 hours. The obtained teeth were bonded with a resin for a denture base (Base Resin Arban, available from K. K. Shofu), the adhesive strength to the base and impact resistance of the artificial teeth by repeated test therefor.

Evaluation of Artificial Teeth

The adhesive strength and the repeated impact resistance were evaluated and shown in Table 7.

TABLE 7

| | components of enamel | components of dentinal | adhesive strength | | impact resistance | |
|---|---|---|---|---|---|---|
| Examples | portion | portion | 1 | 2 | 1 | 2 |
| 41 | Ex. 29 | Ex. 31 | 24.5 | 23.6 | 30 | 29.5 |
| 42 | Ex. 29 | Ex. 32 | 25.6 | 24.6 | 28.6 | 28 |
| 43 | Ex. 29 | Ex. 33 | 24.6 | 24.9 | 29.5 | 29 |
| 44 | Ex. 29 | Ex. 34 | 25.6 | 25 | 30 | 28.5 |
| 45 | Ex. 29 | Ex. 35 | 24.9 | 25.6 | 29.5 | 29.5 |
| 46 | Ex. 29 | Ex. 36 | 25.8 | 25 | 29.5 | 29 |
| 47 | Ex. 29 | Ex. 37 | 24.9 | 24.8 | 30 | 29 |
| 48 | Ex. 29 | Ex. 38 | 26.6 | 26 | 28.6 | 28.5 |

TABLE 7-continued

| | components of enamel | components of dentinal | adhesive strength | | impact resistance | |
|---|---|---|---|---|---|---|
| Examples | portion | portion | 1 | 2 | 1 | 2 |
| 49 | Ex. 29 | Ex. 39 | 28.9 | 25 | 29.5 | 28.5 |
| 50 | Ex. 30 | Ex. 40 | 26.3 | 26 | 28.5 | 29 |
| 51 | Ex. 30 | Ex. 31 | 25.6 | 25 | 30 | 28.5 |
| 52 | Ex. 30 | Ex. 32 | 25.8 | 25 | 30 | 29 |
| 53 | Ex. 30 | Ex. 33 | 25.7 | 25.8 | 30 | 27.9 |
| 54 | Ex. 30 | Ex. 34 | 25.8 | 25.4 | 29.5 | 28.5 |
| 55 | Ex. 30 | Ex. 35 | 25.9 | 25 | 27.5 | 26.5 |
| 56 | Ex. 30 | Ex. 36 | 25.6 | 25 | 29.5 | 28 |
| 57 | Ex. 30 | Ex. 37 | 25.9 | 25.4 | 28.5 | 27.5 |
| 58 | Ex. 30 | Ex. 38 | 26 | 25.1 | 29.5 | 28 |
| 59 | Ex. 30 | Ex. 39 | 26.8 | 25.1 | 28.5 | 27 |
| 60 | Ex. 30 | Ex. 40 | 24.9 | 25 | 28.9 | 27 |
| Resin tooth of Shofu (commertially available) | | | 15.1 | 12.5 | 21.3 | 18.5 |

3) unit: kgf

In Table 7 the adhesive strength-1 was determined after the test piece was held in water of 50° C. for one day, and the adhesive strength-2 was determined after it was kept in water of 50° C. for 7 days. The impact resistance-1 was the data obtained after kept in 50° C. for one day, and impact resistance-2 was the data obtained after subjected with 3000 times of thermal cycles.

As apparent from the results of Examples 41–60 the impact resistance is improved in comparison with commercial products.

A cured article obtained from a dental curable composition of the present invention comprising the silane-treated silica uniformely dispersed in urethane (meth)acrylate as a main component has excellent transparency, toughness, processability (moldability), aesthetic property and wear resistance. In addition, the cured article having an excellent transparency, toughness, processability (moldability), aesthetic property and wear resistance can be obtained by the co-use of the poly(alkly (meth)acrylate) and polymerizable monomer, and is particularly useful as an artificial tooth and a dental crown restorative material.

What is claimed is:

1. A dental curable composition comprising:
   a component which consists essentially of an urethane (meth)acrylate and a silane treated colloidal silica uniformly dispersed holding the state of non-agglomerated primary particle therein, which is obtained by a process comprising the steps of:
   treating a colloidal silica having an average primary particle size of from 1 to 85 nm with at least one silane compound represented by formula (I):

$Y_nSiX_{n-4}$ 

wherein Y is a hydrocarbon group or a reactive group containing a vinyl polymerizable group; X is a hydrolyzable group; and n is an integer of 1, 2, or 3; and dispersing the silane-treated silica in the urethane (meth) acrylate uniformly.

2. A dental curable composition of claim 1, in which the component consists essentially of urethane (meth)acrylate 29–69% by weight, colloidal silica 10–70% by weight and silane compounds 1–30% by weight.

3. A dental curable composition of claim 1 in which the urethane (meth)acrylate contains two or more urethane groups and two or more acryloyl groups and/or methacryloyl groups in one molecule.

4. A dental curable composition of claim 1 further comprising
(b) a polymerizable monomer
(c) a poly(alkyl(meth)acrylate) and
(d) a polymerization initiator.

5. A material for a tooth or a dental crown restoration obtained from the dental curable composition of claim 1.

6. An artificial tooth having three portions composed of
(A) an enamel portion comprising:
(a) the component of claim 1,
(b) a polymerizable monomer,
(c) a poly(alkyl(meth)acrylate) and
(d) a polymerization initiator,
(B) a dentinal portion comprising the above (b), (c), (d) and
(e) a homogeneous component consisting of homogeneously mixed poly(alkyl) acrylate, which is identical to (c), and an urethane (meth)acrylate, and
(C) a base portion comprising the above (b), (c) and (d).

7. An artificial tooth of claim 6, in which the urethane (meth)acrylate is selected from the group consisting of 7,7,9-trimethyl-4,13-dioxo-3,14-dioxo-5,12-diazahexadecane-1,16-diol dimethacrylate (UDMA), 1,6-bis[(2-phenoxy-2'-acryloxy)isopropyl-oxy-carbonylamino]hexane (UDA), 1,1,1-tri[6[(1-acryloxy-3-phenoxy)isopropyloxycarbonylamino]-hexylcarbamoyloxymethyl]propane (URO), compounds represented by formula:

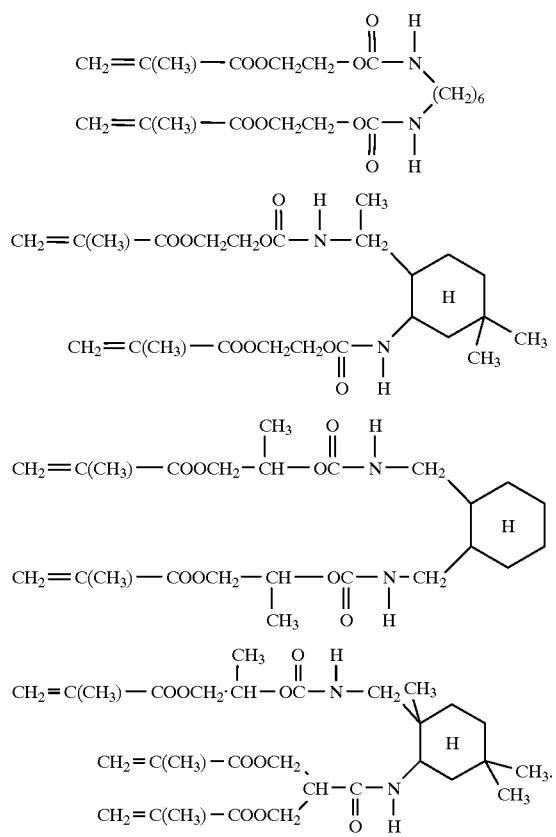

8. An artificial tooth of claim 6, in which the homogeneous component (e) is obtained by a process comprising the step of:

reacting an isocyanate with a homogeneous mixture of the poly(alkyl(meth)acrylate) and a hydroxyl group containing (meth)acrylate.

9. An artificial tooth of claim 6, in which the homogeneous component (e) is obtained by a process comprising the step of:

reacting a hydroxyl group-containing (meth)acrylate with a homogeneous mixture of the poly(alkyl(meth)acrylate) and an isocyanate.

10. An artificial tooth of claim 6, in which the homogeneous component (e) is obtained by a process comprising the step of:

(1) reacting a homogeneous mixture of the poly(alkyl(meth)acrylate) and an isocyanate with a polyol having hydroxyl groups of 2–4 to provide a polyisocyanate, and then (2) reacting the polyisocyanate and a hydroxyl group containing (meth)acrylate.

11. A dental curable composition of claim 2, in which the urethane (meth)acrylate contains two or more urethane groups and two or more acryloyl groups and/or methacryloyl groups in one molecule.

12. A dental curable composition of claim 2 which comprises,
(a) the component of claim 1, 34–68% by weight,
(b) a polymerizable monomer 17–51% by weight, and
(c) a poly(alkyl(meth)acrylate) 15–20% by weight, and additionally
(d) a polymerization initiator 0.1–3.0% by weight based on the total weight of (a), (b) and (c).

13. A dental curable composition of claim 3 which comprises,
(a) the component of claim 1, 34–68% by weight,
(b) a polymerizable monomer 17–51% by weight, and
(c) a poly(alkyl(meth)acrylate) 15–20% by weight, and additionally
(d) a polymerization initiator 0.1–3.0% by weight based on the total weight of (a), (b) and (c).

14. A material for a tooth or a dental crown restoration obtained from the dental curable composition of claim 2.

15. A material for a tooth or a dental crown restoration obtained from the dental curable composition of claim 3.

16. A dental curable composition of claim 1, in which the component shows equal to or more than 80% of light transmittance at 750–380 nm both before and after curing the component.

17. A dental curable composition of claim 4 which comprises,
(a) the component, 34–68% by weight,
(b) a polymerizable monomer 17–51% by weight; and
(c) a poly(alkyl(meth)acrylate) 15–20% by weight, and additionally,
(d) a polymerization initiator 0.1–3.0% by weight based on the total of (a), (b) and (c).

18. A material for a tooth or a dental crown restoration obtained from the dental curable composition of claim 17.

19. A dental curable composition of claim 1, in which said composition shows equal to or more than 80% of light transmittance at 750–380 nm both before and after curing the composition.

* * * * *